United States Patent
Xu et al.

(10) Patent No.: US 6,403,354 B1
(45) Date of Patent: Jun. 11, 2002

(54) **METHOD FOR CLONING AND EXPRESSION OF BSTYI RESTRICTION ENDONUCLEASE AND BSTYI METHYLASE IN *E. COLI* AND PURIFICATION OF BSTYI AND M.BSTYI ENZYMES**

(75) Inventors: Shuang-yong Xu, Lexington; James Samuelson, Danvers; John Pelletier, Amesbury; Marion Sibley, Beverly; Geoffrey G. Wilson, Boxford, all of MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/766,055

(22) Filed: Jan. 19, 2001

(51) Int. Cl.⁷ .............................. C12N 9/22; C12N 15/55
(52) U.S. Cl. ................. 435/199; 435/252.3; 435/320.1; 536/23.2
(58) Field of Search .............................. 435/199, 252.3, 435/320.1; 536/23.2

(56) References Cited

U.S. PATENT DOCUMENTS

| 5,200,333 A | 4/1993 | Wilson ..................... 435/172.3 |
| 5,498,535 A | 3/1996 | Fomenkov ............... 435/172.3 |

OTHER PUBLICATIONS

Blumenthal, et al., J. Bacteriology 164:501–509 (1985).
Bougueleret, et al. Nucl. Acids Res. 12:3659–3676 (1984).
Fomenkov, et al., Nucl. Acids Res. 22:2399–2403 (1994).
Gingeras and Brooks, Proc. Natl. Acad. Sci. USA 80:402–806 (1983).
Janulaitis, et al., Gene 20:197–204 (1982).
Kiss and Baldauf, Gene 21:111–119 (1983).
Kiss, et al., Nucl. Acids Res. 13:6403–6421 (1985).
Kosykh, et al., Mol. Gen. Genet. 178:717–718 (1980).
Malone, et al., J. Mol. Biol. 253:618–632 (1995).
Maniatis, et al. Molecular Cloning: A Laboratory Manual, p. 93–94 (1982).
Mann, et al., Gene 3:97–112 (1978).
New England Biolabs, Inc. 2000–2001 Catalog, p. 220.
Roberts and Macelis, Nucl. Acids Res. 27–312–313 (1999).
Szomolanyi, et al., Gene 10:219–225 (1980).
Theriault and Roy, Gene 19:355–359 (1982).
Walder, et al., J. Biol. Chem. 258:1235–1241 (1983).
Walder, et al., Proc. Natl. Acad. Sci. 78:1503–1507 (1981).
Wayne, et al., Gene 202:83–88 (1997).

*Primary Examiner*—Charles L. Patterson, Jr.
(74) *Attorney, Agent, or Firm*—Gregory D. Williams (57) ABSTRACT

The present invention relates to recombinant DNA which encodes the BstYI restriction endonuclease as well as BstYI methyltransferase, expression of BstYI restriction endonuclease and M.BstYI in *E. coli* cells containing the recombinant DNA. It also relates to methods for purification of the recombinant BstYI restriction endonuclease and BstYI methyltransferase.

6 Claims, 5 Drawing Sheets

FIG. 1

BstYI RESTRICTION-MODIFICATION SYSTEM

RECOGNITION SEQUENCE 5'Pu^GATCPy 3'

FIG. 2

```
    ATGAACTTCTTGAGTCTATTTGAATATAGAATTGATGATGTTTATAAGGAAGATAGCGAA
1   ------------+---------+---------+---------+---------+---------+  60
    M  N  F  L  S  L  F  E  Y  R  I  D  D  V  Y  K  E  D  S  E
    ATTGTATTTCATAACGGCGATGCGCTTGAGTTTTTGAAAACATTACCCGATAATCTTGTG
61  ------------+---------+---------+---------+---------+---------+  120
    I  V  F  H  N  G  D  A  L  E  F  L  K  T  L  P  D  N  L  V
    AAATTAGCGATCACGTCCCCGCCTTATAACGTTGGTAAGTCTTATGAAGTAAAAACGTCA
121 ------------+---------+---------+---------+---------+---------+  180
    K  L  A  I  T  S  P  P  Y  N  V  G  K  S  Y  E  V  K  T  S
    GTTGAAGAATATCTTGCAACACAAGAAGCCGTAATTGAAGAATTGATTCGGGTCGTTGAT
181 ------------+---------+---------+---------+---------+---------+  240
    V  E  E  Y  L  A  T  Q  E  A  V  I  E  E  L  I  R  V  V  D
    GATCACGGAAGCATTTGTTGGCAAGTGGGAAACTATGTTAATAAAGGAGAAATTTTTCCG
241 ------------+---------+---------+---------+---------+---------+  300
    D  H  G  S  I  C  W  Q  V  G  N  Y  V  N  K  G  E  I  F  P
    CTTGATATATTTTATTATCAAATCTTCAAAAAACATGGTTTGAAACTTCGGAACCGTATC
301 ------------+---------+---------+---------+---------+---------+  360
    L  D  I  F  Y  Y  Q  I  F  K  K  H  G  L  K  L  R  N  R  I
    ATTTGGCATTTTGGTCACGGTCTTCACGCAAAGAAACGCTTTTCGGGAAGATATGAGACA
361 ------------+---------+---------+---------+---------+---------+  420
    I  W  H  F  G  H  G  L  H  A  K  K  R  F  S  G  R  Y  E  T
    TTGCTTTGGTTCACGAAATCAGATGATTACACTTTTAACCTTGACCCCGTTCGGGTTCCT
421 ------------+---------+---------+---------+---------+---------+  480
    L  L  W  F  T  K  S  D  D  Y  T  F  N  L  D  P  V  R  V  P
    GCAAAGTATCCCGGCAAACGTCATTATAAAGGTGACAAAAAAGGCGAACTATCGGGGAAT
481 ------------+---------+---------+---------+---------+---------+  540
    A  K  Y  P  G  K  R  H  Y  K  G  D  K  K  G  E  L  S  G  N
    CCGAAAGGAAAAAATCCTTCGGACGTATGGGAATTCGTTGTTCAAGAATGGGACAAGGAA
541 ------------+---------+---------+---------+---------+---------+  600
    P  K  G  K  N  P  S  D  V  W  E  F  V  V  Q  E  W  D  K  E
    CTTTGGGAAATTCCGAACGTGAAGGCGAATCACCCCGAAAAAACAATTCACCCGTGTCAA
601 ------------+---------+---------+---------+---------+---------+  660
    L  W  E  I  P  N  V  K  A  N  H  P  E  K  T  I  H  P  C  Q
    TATCCGATTGAATTGGTTGAACGTTGTGTTTTAGCATTAACGAATGAAAATGACTTTGTT
661 ------------+---------+---------+---------+---------+---------+  720
    Y  P  I  E  L  V  E  R  C  V  L  A  L  T  N  E  N  D  F  V
    CTTGACCCGTATGCGGGTGTTGGTTCGTCGTTGATTGGTGCATTGAAACATGGAAGAAAA
721 ------------+---------+---------+---------+---------+---------+  780
    L  D  P  Y  A  G  V  G  S  S  L  I  G  A  L  K  H  G  R  K
    GCAATCGGTGTTGATAAAGAGAAAGAATACGTTGAGATTGGAAAACAAAGAATCAAAGAT
781 ------------+---------+---------+---------+---------+---------+  840
    A  I  G  V  D  K  E  K  E  Y  V  E  I  G  K  Q  R  I  K  D
    TTCTATGACGGTAAATTAAAGATTAGACCGTTAGGAAAACCCGTTTACCAACCAACGGGA
841 ------------+---------+---------+---------+---------+---------+  900
    F  Y  D  G  K  L  K  I  R  P  L  G  K  P  V  Y  Q  P  T  G
    AGAGAAAAGGTTGCACAAATTCCTGAAGAATGGAAAGAACTCCTAGAACAAAAGTAA
901 ------------+---------+---------+---------+---------+------  957
    R  E  K  V  A  Q  I  P  E  E  W  K  E  L  L  E  Q  K  *
```

FIG. 3

```
    ATGAGAATTGTTGAAGTATATTCGCATTTGAACGGGTTGGAATACATACAAGTTCACTTG
  1 ---------+---------+---------+---------+---------+---------+  60
    M  R  I  V  E  V  Y  S  H  L  N  G  L  E  Y  I  Q  V  H  L
    CCACATATTTGGGAAGAAATTCAAGAAATTATTGTTTCTATTGACGCAGAAGCTTGTAGA
 61 ---------+---------+---------+---------+---------+---------+ 120
    P  H  I  W  E  E  I  Q  E  I  I  V  S  I  D  A  E  A  C  R
    ACGAAGGAATCAAAAGAAAAGACAAAACAAGGACAAATACTTTATAGTCCCGTAGCTTTA
121 ---------+---------+---------+---------+---------+---------+ 180
    T  K  E  S  K  E  K  T  K  Q  G  Q  I  L  Y  S  P  V  A  L
    AATGAAGCATTCAAGGAAAAATTAGAAGCAAAAGGTTGGAAAGAAAGTCGAACAAACTAT
181 ---------+---------+---------+---------+---------+---------+ 240
    N  E  A  F  K  E  K  L  E  A  K  G  W  K  E  S  R  T  N  Y
    TATGTGACTGCTGACCCAAAGCTGATTCGTGAAACATTATCACTTGAACCAGAGGAACAA
241 ---------+---------+---------+---------+---------+---------+ 300
    Y  V  T  A  D  P  K  L  I  R  E  T  L  S  L  E  P  E  E  Q
    AAGAAAGTGATTGAAGCCGCAGGAAAAGAAGCATTAAAGTCTTATAATCAAACGGATTTT
301 ---------+---------+---------+---------+---------+---------+ 360
    K  K  V  I  E  A  A  G  K  E  A  L  K  S  Y  N  Q  T  D  F
    GTAAAAGATAGAGTGGCAATAGAAGTTCAATTCGGAAAATATTCTTTTGTCGCTTATGAC
361 ---------+---------+---------+---------+---------+---------+ 420
    V  K  D  R  V  A  I  E  V  Q  F  G  K  Y  S  F  V  A  Y  D
    CTTTTCGTCAAACATATGGCTTTCTATGTTAGTGATAAAATTGACGTTGGTGTCGAAATA
421 ---------+---------+---------+---------+---------+---------+ 480
    L  F  V  K  H  M  A  F  Y  V  S  D  K  I  D  V  G  V  E  I
    TTGCCAATGAAGGAATTATCAAAAGAAATGTCTTCGGGAATCAGTTATTACGAAGGTGAA
481 ---------+---------+---------+---------+---------+---------+ 540
    L  P  M  K  E  L  S  K  E  M  S  S  G  I  S  Y  Y  E  G  E
    TTATACAATGTGATACGGCAAGGTCGTGGCGTTCCTGCCGTTCCGTTGGTTTTAATCGGG
541 ---------+---------+---------+---------+---------+---------+ 600
    L  Y  N  V  I  R  Q  G  R  G  V  P  A  V  P  L  V  L  I  G
    ATTGCCCCTTAA
601 ----------+-- 612
    I  A  P  *
```

METHOD FOR CLONING AND EXPRESSION OF BSTYI RESTRICTION ENDONUCLEASE AND BSTYI METHYLASE IN *E. COLI* AND PURIFICATION OF BSTYI AND M.BSTYI ENZYMES

BACKGROUND OF THE INVENTION

The present invention relates to recombinant DNA which encodes the BstYI restriction endonuclease (endonuclease) as well as BstYI methyltransferase (methylase), expression of BstYI restriction endonuclease and methylase in *E. coli* cells containing the recombinant DNA.

BstYI endonuclease is found in the strain of *Bacillus stearothermophilus* Y406 (New England Biolabs' strain collection #434). It recognizes the double-stranded DNA sequence 5'Pu/GATCPy3' and cleaves between the Pu and G to generate a 4-base 5' overhanging ends (Pu=A or G; Py=T or C;/indicates the cleavage of phosphodiester bond). BstYI methylase (M.BstYI) is also found in the strain of *Bacillus stearothermophilus* Y406. It recognizes the double-stranded DNA sequence 5'PuGATCPy3' and modifies the N4-cytosine by addition of a methyl group to become N4-methylcytosine in the DNA sequence. The N4mC modified BstYI site is resistant to BstYI restriction digestion.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along the DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3', 5'PuG/GNCCPy3' and 5'CACNNN/GTG3' respectively. *Escherichia coli* RY13, on the other hand, produces only one enzyme, EcoRI, which recognizes the sequence 5'G/AATTC3'.

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., Mol. Gen. Genet. 178:717–719, (1980); HhaII: Mann et al., Gene 3:97–112, (1978); PstI: Walder et al., Proc. Nat. Acad. Sci. 78:1503–1507, (1981)). Since the expression of restriction-modification systems in bacteria enable them to resist infection by bacteriophage, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., Nucl. Acids. Res. 12:3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne et al. Gene 202:83–88, (1997)).

A third approach is to select for active expression of methylase genes (methylase selection) (U.S. Pat. No. 5,200,333 and BsuRI: Kiss et al., Nucl. Acids. Res. 13: 6403–6421, (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baldauf, Gene 21:111–119, (1983); and MspI: Walder et al., J. Biol. Chem. 258:1235–1241, (1983)).

A more recent method, the "endo-blue method", has been described for direct cloning of thermostable restriction endonuclease genes into *E. coli* based on the indicator strain of *E. coli* containing the dinD::lacZ fusion (Fomenkov et al., U.S. Pat. No. 5,498,535, (1996); Fomenkov et al., Nucl. Acids Res. 22:2399–2403, (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535, 1996). The disadvantage of this method is that sometimes positive blue clones containing a restriction endonuclease gene are difficult to culture due to the lack of the cognate methylase gene.

There are three major groups of DNA methyltransferases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632, (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5'CCWGG3' (W=A or T) can also make the DNA resistant to PspGI restriction digestion. Another example is that CpM methylase can modify the CG dinucloetide and make the NotI site (5'GCGGCCGC3') refractory to NotI digestion (New England Biolabs' Catalog, 2000–01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a strong commercial interest to obtain bacterial strains through recombinant DNA techniques that produce large quantities of restriction enzymes. Such over-expression strains should also simplify the task of enzyme purification.

SUMMARY OF THE INVENTION

The present invention relates to a method for cloning the BstYI restriction endonuclease from *Bacillus stearothermophilus* into *E. coli* by methylase selection and inverse PCR amplification of the adjacent DNA. A methylase gene with high homology to amino-methyltransferases (N4-cytosine methylases) was found in a DNA library after methylase selection. This gene was named BstYI methylase gene (bstYIM).

In order to clone the BstYI endonuclease gene in a large DNA fragment, partial HindIII genomic DNA fragment libraries were constructed using vectors pBR322 and pUC19. More methylase positive clones were obtained. However, no endonuclease activity was detected in all M.BstYI positive clones.

To ensure there was sufficient DNA coding capacity on both sides of the bstYIM gene, a Southern blot analysis was performed to generate a restriction map near the bstYIM gene. Restriction mapping indicated that ClaI, NsiI, PvuII, and SphI fragments would have DNA large enough to encode the bstYIR gene on either side. Again, methylase positive clones were derived from the new libraries, but no endonuclease activity was detected in cell extract or purified cell extract fractions. More than 14 kb of DNA was derived from one side of the bstYIM. It was extremely difficult to obtain DNA on the other side of bstYIM. The DNA fragment that was difficult to clone simultaneously with bstYIM gene might contain the bstYIR gene.

To screen for DNA damage induced by expression of the BstYI endonuclease or methylation dependent restriction systems, primary plasmid library DNA was used to transform into a dinD::lacZ fusion strain AP1-200 and plated on X-gal plates. A number of blue colonies were found, but none of them contained the BstYI endonuclease gene.

Since both methylase selection and SOS induction assays failed to yield a BstYI endonuclease clone, inverse PCR was employed to amplify the adjacent downstream DNA sequence. An open reading frame was found adjacent to the bstYIM gene. This ORF was named bstYIR and expressed in a T7 expression vector pET21b. This clone produced more than $10^6$ units of BstYI per gram of cells. However, this clone was unstable due to a high expression level under non-induced conditions. To construct a more stable clone, an internal NdeI site was mutagenized and the bstYIR gene (an NdeI-XhoI fragment) was then inserted into a T7 expression vector with 4 copies of a transcription terminator upstream of the T7 promoter.

To overexpress the bstYIM gene, the gene was amplified by PCR and cloned into expression vector TYB2. The M.BstYI was expressed as a fusion to chitin binding domain and intein. The host ER2566 (an *E. coli* B strain) was found to be intolerant to overexpression of M.BstYI and gave a low yield of M.BstYI protein. The plasmid TYB2-BstYIM was later transferred into *E. coli* K strain ER1821(λDE3), a strain deficient in methylation dependent restriction systems (McrBC⁻ McrA⁻, Mrr⁻). The M.BstYI protein was purified by chromatography through affinity, anion exchange, and cation exchange columns.

BRIEF DESCRIPTION OF THE DRAWINGS

FIG. 2. DNA sequence of BstYI methylase gene (SEQ ID NO:1) (bstYIM, 957 bp) and its encoded amino acid sequence (SEQ ID NO:2).

DETAILED DESCRIPTION OF THE INVENTION

The method described herein by which the BstYI methylase gene and the BstYI restriction endonuclease genes are preferably cloned and expressed in *E. coli* using the following steps:

1. Construction of Genomic DNA Libraries and Methylase Selection

Genomic DNA is prepared from *Bacillus stearothermophilus* Y406 (strain source from Professor Xingshi Pan;

Institute of Genetics; Fudan University; Shanghai, 200433 People's Republic of China) and digested with restriction enzymes such as BclI, EcoRI, HindIII, PstI, and Sau3AI partially or completely. The restricted genomic DNA is ligated to E. coli cloning/expression vectors such pUC19 or pBR322 with compatible ends. The ligated DNA is transformed into restriction minus E. coli competent cells such as RR1 and transformants are pooled and amplified. Plasmid DNA libraries are prepared and challenged with BstYI or any isoschizomer. Following digestion, the plasmids are transformed back into RR1 cells. $Ap^R$ or $Tc^R$ survivors are screened for resistance to BstYI digestion. The resistant clones are identified as methylase positive clones or plasmids that had simply lost the restriction sites. Sequencing the insert (skip to step 5) verified the cloning of a methylase gene.

2. Selection of More M.BstYI Positive Clones

Because a restriction endonuclease gene is usually located in close proximity to a methylase gene, efforts can be made to construct more genomic DNA libraries that contain larger genomic DNA inserts. Genomic DNA is digested partially with 6–8 bp cutting enzymes such HindIII and ligated to pBR322. The ligated DNA is transformed into RR1 cells and plasmid DNA is prepared and challenged with BstYI or any isoschizomer. Following this approach, additional M.BstYI positive clones were derived. BstYI endonuclease activity assays were carried out using cells extracts of the $M^+$ clones. If no BstYI endonuclease positive clones are found, go to step 3.

3. Restriction Mapping of the Surrounding DNA of bstYIM gene and Construction of More Genomic DNA Libraries B. stearothermophilus Y406 genomic DNA was digested with endonucleases with 6–8 bp recognition sequences to identify DNA fragments that encompass the bstYIM gene and the flanking DNA. In a Southern blot analysis it was found that four enzymes (ClaI, NsiI, PvuI, and SphI) would generate large DNA fragments carrying adjacent DNA either side of the bstYIM gene.

B. stearothermophilus Y406 genomic DNA was digested with ClaI, NsiI, PvuI, and SphI respectively or any other enzymes that generate large fragments. Genomic DNA libraries were constructed using pUC and pBR328 vectors. More M.BstYI positive clones were derived from the four libraries. The adjacent upstream DNA was extended further for at least 14 kb. However, no endonuclease activity was detected among these M.BstYI positive clones. The adjacent downstream sequence proved to be extremely difficult to clone indicating a toxic gene effect. It was postulated that the adjacent downstream sequence may encode the bstYIR gene.

4. Screening Nuclease-containing Clone by dinD::lacZ Indicator Strain

ClaI, EcoRI, NsiI, PvuI, and SphI genomic DNA libraries were transformed into a dinD::lacZ indicator strain AP1-200 or any DNA damage inducible gene fused with a reporter gene. If a plasmid carries a nuclease gene (endonuclase, exonuclease, integrase, or gyrase), the gene product may induce an SOS response and increase the expression of dinD::lacZ fusion (production of β-galactosidase). The colony carrying such a plasmid would turn blue on an X-gal plate. Some blue colonies were found among the transformants, but none of them carried the bstYIR gene.

5. Sequencing of bstYIM Gene

The bstYIM gene is sequenced by insertion of priming sites of GPS-1 genome priming system or by primer walking. The bstYIM gene is 957 bp, encoding a 318-aa protein with predicted molecular mass of 36.9 kDa.

6. Cloning of bstYIM Gene into pACYC184 to Construct a Premodified Host

The bstYIM gene was amplified from the genomic DNA by PCR using two primers. The PCR DNA was digested with BamHI and SphI and ligated to low/medium copy number plasmids such as pACYC184 that are compatible with pET T7 expression vectors. The premodified host ER2744 [pACYC-BstYIM] was used for expression of the bstYIR gene in E. coli.

7. Expression of M.BStYI as a Fusion to Chitin Binding Domain and Itein and Purification of M.BstYI Through Affinity Chromatography.

The bstYIM gene was amplified from the genomic DNA by PCR. The PCR product was digested with NdeI and ligated to NdeI and SmaI cut TYB2 vector. The expression strain ER2566 [TYB2-BstYIM] was cultured and induced. Protein in the cell extract was purified through a chitin column and DTT cleavage. The purified M.BstYI protein was analyzed by SDS-PAGE. The protein was the correct size of 36.9 kDa. However, the M.BstYI protein yield was rather low, resulting in only partial BstYI site modification. In order to increase the level of M.BstYI expression, the expression vector was introduced into an E. coli K strain T7 expression host such as ER1821(λDE3). The expression level in the K-12 strain was significantly higher than that in the B strain ER2566.

8. Purification of M.BstYI by Chromatography

The cell extract containing M.BstYI was fractionated by affinity chromatography using a chitin column and Heparin TSK column. M.BstYI protein can be further purified through cation or anion exchange columns. Lambda DNA or any other substrate with BstYI sites can be first modified by M.BstYI in a methylation buffer. After methylation of the substrate, the DNA can be assayed for protection against BstYI restriction. When the DNA is modified by M.BstYI, the DNA should become resistant to BstYI digestion.

9. Cloning of bstYIR Gene by Inverse PCR

The Genomic DNA was digested with 4–6 bp cutting restriction enzymes such as AciI, BfaI, BspHI, EcoRI, HhaI, HpyIV, MseI, and NlaIII. The digested DNA was ligated at a low DNA concentration and then used for inverse PCR amplification of the bstYIR gene. Inverse PCR products were derived and sequenced. An ORF of 612 bp was found downstream of the bstYIM gene. This ORF is named bstYIR gene. It encodes a 203-aa protein with predicted molecular mass of 23 kDa.

10. Expression of bstYIR Gene in T7 Expression Vector pET21b

Because there is an NdeI site in the bstYIR gene, the NdeI site cannot be used for cloning of bstYIR gene into pET21b expression vector. The XbaI and XhoI sites were incorporated into the forward primer and reverse primers. A ribosome binding site was also engineered into the forward primer.

The bstYIR gene is amplified by PCR using a proofreading DNA polymerase such as Vent® DNA polymerase (New England Biolabs, Inc., Beverly, mA) and primers. The PCR product was digested with XbaI and XhoI. and ligated to expression vector such as pET21b. The ligated DNA was transformed into premodified host ER2744 [pACYC-BstYIM]. Plasmids with the correct size insert were screened from the $Ap^R$ $Cm^R$ transformants. Cell extracts were prepared and assayed for BstYI activity. One clone #11 displayed high BStYI activity. However, this expression clone was unstable due to loss of activity after subculture of cell stocks. The reason of instability was probably due to the high level of expression under non-induced condition. The bstYIR gene was inserted into the XbaI and XhoI sites of pET21b. The XbaI site is 3-bp away from the lac operator sequence that Lac repressor binds. For some unknown reason, the insertion of bstYIR gene at the XbaI site interfered with Lac repression. Efforts were made to construct a new expression clone.

11. Introduction of a Silent Mutation in bstYIR Gene to Eliminate an Internal NdeI Site T7 expression vectors usually contain NdeI or NcoI sites for cloning of 5' start codon side of the target gene. The ATG start codon is contained within the NdeI site (5'CATATG3') or the NcoI site (5'CCATGG3'). An efficient ribosome binding site (translation signal) is located upstream of the NdeI or NcoI site. In order to clone the bstYIR gene into a T7 expression vector, an internal NdeI site within the bstYIR gene had to be eliminated by mutagenesis. Overhang extension PCR was performed to remove the NdeI site. The first 449-bp of the gene was amplified using 5' forward and internal reverse mutagenic primers. The second part of the gene was amplified with internal forward mutagenic and 3' reverse primers. The two PCR products were purified and further amplified by the 5' forward and 3' reverse primers. Alternatively, one can use oligonucleotide-directed mutagenesis using single-stranded DNA template to perform the mutagenesis and then clone the gene into a T7 expression vector such as pET21at. The vector pET21at contains 4 copies of transcription terminators upstream of T7 promoter and thus run-off transcriptions from cryptic *E. coli* promoters can be terminated. One can also engineer other restriction sites in the 5' and 3' end of bstYIR gene and a ribosome binding site (translation signal) following the 5' restriction site and before ATG start codon.

12. Expression of bstYIR Gene in T7 Expression Vector pET21at

The bstYIR gene PCR product was digested with NdeI and XhoI and ligated to pET21at or any other T7 expression vectors with appropriate restriction sites or any *E. coli* expression vectors with tightly-controlled promoters. The ligated DNA was transformed into premodified host ER2744 [pACYC-BstYIM, pCEF8] and transformants were selected. Alternatively, one can use M.BstYI isoschizomer such as M.XhoII to premodify *E. coli* host. One clone was found to contain the wild type bstYIR coding sequence and the desired silent mutation at the internal NdeI site.

13. Purification of BstYI Endonuclease by Chromatography

Cell extract containing the recombinant BstYI endonuclease was heated at 65° C. for 30 min and the heat-denatured proteins were removed by centrifugation. BstYI endonuclease was further purified by chromatography through Heparin-Sepharose and DEAE-Sepharose columns. Alternatively, BstYI endonuclease can be purified by chromatography through cation/anion exchange columns and gel filtration sizing columns or by affinity purification through fusion tags such as His tag, GST tag, chitin binding domain tag, MBP binding domain tag.

The present invention is further illustrated by the following Examples. These Examples are provided to aid in the understanding of the invention and are not construed as a limitation thereof.

The references cited above and below are herein incorporated by reference.

EXAMPLE 1

Cloning of BstYI Restriction-modification System in *E. coli*

1. Preparation of Genomic DNA and Restriction Digestion of Genomic DNA

Genomic DNA was prepared from *Bacillus stearothermophilus* Y406 (New England Biolabs collection #434) by the standard procedure consisting of the following steps:

a) cell lysis by addition of lysozyme (2 mg/ml final), sucrose (1% final), and 50 mM Tris-HCl, pH 8.0.

b) cell lysis by addition of 10% SDS (final concentration 0.1%).

c) cell lysis by addition of 1% Triton X-100 and 62 mM EDTA, 50 mM Tris-HCl, pH 8.0.

d) phenol-$CHCl_3$ extraction of DNA 3 times (equal volume) and $CHCl_3$ extraction once.

e) DNA dialysis in 4 liters of TE buffer, change 3 times.

f) RNA was removed by RNase A treatment and the genomic DNA was precipitated in 95% ethanol, spooled, washed, and resuspended in TE buffer.

Restriction enzymes BclI, EcoRI, HindIII, PstI, and Sau3AI were diluted by 2-fold serial dilutions. Five to ten µg genomic DNA was digested partially or completely with BclI, EcoRI, HindIII, or PstI at 37° C. for 30 min. The genomic DNA was also partially digested with Sau3AI. The BclI and Sau3AI digested genomic DNA was ligated to BamHI digested and CIP treated pUC19 vector. The EcoRI, HindIII, and PstI digested genomic DNA was ligated to CIP-treated pUC19 with compatible ends. PstI digested genomic DNA was also ligated to pBR322 with compatible ends. The ligated DNA was used to transform *E. coli* RR1 competent cells by the standard procedure.

2. Construction of BCII, HindIII, PstI Partial and Complete Genomic DNA Libraries and Sau3AI Partial Genomic DNA Library and Selection of M.BstYI by the Methylase Selection Method For the transformation experiment the antibiotic ampicillin (Ap) was used to select transformants of BclI, EcoRI, HindIII, PstI, and Sau3AI libraries. Tetracycline (Tc) was used to select pBR322+PstI genomic fragment library. A total of more than $2\times10^4$ $AP^R$ and $2.6\times10^3$ $Tc^R$ transformants were obtained in two transformation experiments. These transformants were pooled and amplified in 1 liter of overnight cultures. Plasmid DNA was prepared from the overnight cells by the CsCl ultracentrifugation method (Maniatis et al. in Molecular Cloning, page 93). The plasmid libraries were challenged with BstYI for 3 h at 60° C. Following BstYI digestion, the challenged DNA was transformed back into RR1 competent cells. $AP^R$ or $Tc^R$ survivors were screened for resistance to BstYI digestion. A total of 118 plasmid mini-preparations were made. Thirty-two clones were identified to be partially resistant to BstYI digestion. All the resistant clones (M.BstYI positive) were derived from HindIII complete/partial libraries. A 1.3 kb fragment insert was common among all the $M^+$ clone. It was concluded that the 1.3 kb fragment must contain the bstYIM gene. (Later, when the insert was sequenced, it was confirmed that it encodes the M.BstYI. see section 5 below).

3. Selection of More M.BstYI Positive Clones

Because a restriction gene is usually located in close proximity to the cognate methylase gene more genomic DNA libaries were constructed that contained larger genomic DNA inserts. *B. stearothermophilus* Y406 genomic DNA was digested partially with HindIII and ligated to CIP-treated pBR322 with compatible ends. The ligated DNA was transformed into RR1 competent cells and plasmid DNA was prepared and challenged with BstYI endonuclease. Seven more M.BstYI positive clones were derived from the HindIII library, but no BstYI endonuclease positive clones were found.

4. Restriction Mapping of the Flanking DNA of bstYIM Gene and Construction of More Genomic DNA Libraries

*B. stearothermophilus* Y406 genomic DNA was digested with restriction enzymes with 6-bp recognition sequence to identify DNA fragments that encompass bstYIM gene and the flanking DNA. The genomic DNA was digested with AseI, BclI, BstBI, ClaI, DraI, EcoRI, FspI, NaeI, NdeI, NheI, NsiI, PstI, PvuI, PvuII, ScaI, SphI, SalI, SspI, and XmnI. The genomic DNA fragments were separated in an agarose gel. The DNA was denatured and transferred to a nitrocellulose membrane. The membrane was dried, crosslinked by UV, and hybridized with $^{32}$P-labelled probe of 1.3 HindIII fragment containing bstYIM gene. It was found that four enzymes would generate large DNA fragments carrying adjacent DNA to both sides of the bstYIM gene. The approximate sizes of the DNA fragments were ClaI, 7.2 kb; NsiI, 6.5 kb; PvuI, >16 kb; SphI, 6 kb.

*B. stearothermophilus* Y406 genomic DNA was digested with ClaI, NsiI, PvuI, and SphI respectively. The NsiI and SphI DNA fragments were ligated to CIP-treated pUC vector; ClaI and PvuI genomic fragments were ligated to CIP-treated pBR328 vector. The ligated DNA was transformed into RR1 competent cells and plasmid DNA was prepared and challanged with BstYI endonuclease. Twenty-three more M.BstYI positive clones were derived from the four libraries. The adjacent upstream DNA was extended further for at least 14 kb. However, no endonuclease activity was detected among these M.BstYI positive clones. The adjacent downstream sequence was extremely difficult to clone which indicated a toxic gene effect. It was concluded that the adjacent downstream sequence may encode the bstYIR gene. Cloning of the bstYIR gene may require a M.BstYI premodified host.

5. Screening Nuclease-containing Clone by dinD::lacZ Indicator Strain

ClaI, EcoRI, NsiI, PvuI, and SphI genomic DNA libraries were transformed into a dinD::lacZ indicator strain AP1-200. If the plasmid carries a nuclease gene (for example, endonuclease, exonuclease, integrase, or gyrase), the gene product may induce the SOS response and increase the expression of a dinD::lacZ fusion (production of β-galactosidase). The colony carrying such plasmid would turn blue on an X-gal plate. Some blue colonies were found among the transformants, but none of them displayed BstYI endonuclease activity.

6. Sequencing of bstYIM Gene

The bstYIM gene was sequenced by insertion of priming sites of GPS-1 genome priming system (New England Biolabs). The bstYIM gene is 957 bp, encoding a 318-aa protein with predicted molecular mass of 36.9 kDa. Sequence comparison with other methylases in GenBank indicated that M.BstYI is probably an N4-cytosine methylase. In addition, Dam methylation of the 5'GATC3' site does not confer resistance to BstYI digestion. Dam methylase is an N6 adenine methylase which modifies adenine in the 5'GATC3' sequence.

7. Cloning of bstYIM Gene into pACYC184 to Construct a Premodified Host

Two primers were synthesized with the following sequence:

5' aaaactggatccggaggtaaaaaaatgaacttcttgagtctatttgaatataga 3' (237-61) (SEQ ID NO:5)

5' taacacgcatgcttacttttgttctaggagttctttccattc 3' (235-257) (SEQ ID NO:6)

The bstYIM gene was amplified from the genomic DNA in PCR using primers 237-61 and 235-257 under PCR condition of 94° C. 1 min, 55° C. 1 min, 72° C. 1 min for 20 cycles. The PCR DNA was purified through a Qiagen spin column and digested with BamHI and SphI and ligated to CIP treated pACYC184 with compatible ends. After screening 18 plasmid mini-preparations, 7 clones were found to be resistant to BstYI digestion. The resistant clones were also resistant to BamHI digestion because BamHI sites (5'GGATCC3') are also BstYI sites (5'PuGATCPy3'). The premodified host ER2744 [pACYC-BstYIM] was used for expression of the bstYIR gene in *E. coli*.

8. Expression of M.BstYI as a Fusion to Chitin Binding Domain and Intein and Purification of M.BstYI Through Affinity Chromatography Two primers were synthesized with the following sequence:

5' gtagtgaggcatatgaacttcttgagtctatttgaatataga 3' (234-397) (SEQ ID NO:7).

5' cttttgttctaggagttctttccattc 3' (234-398). (SEQ ID NO:8)

The bstYIM gene was amplified from the genomic DNA in PCR using primers 234-397 and 234-398 under PCR conditions of 94° C. 1 min, 55° C. 1 min, 72° C. 1 min for 20 cycles. The PCR DNA was purified through a Qiagen spin column and digested with NdeI endonuclease. The PCR DNA was purified by spin column again and ligated to NdeI and SmaI cut TYB2 vector. TYB2 is an expression vector with intein cleavage of the fusion protein. The fusion protein can be purified through a chitin affinity column. After screening 18 plasmid mini-preparations, 4 clones were found to be resistant to BstYI digestion, indicating sufficient expression of M.BstYI in vivo under non-induced conditions.

The expression strain ER2566 [TYB2-BstYIM] was cultured in 1 L LB plus Ap and induced with IPTG. Cells were lysed by sonication and cell debris was removed by centrifugation. Protein in the cell extract was loaded onto a chitin column. After extensive washing, the column was flooded with buffer containing 40 mM DTT to facilitate the cleavage of M.BstYI from the fusion protein. Following overnight cleavage, the M.BstYI protein was eluted in an elution buffer (500 mM NaCl, 20 mM Tris-HCl, 1 mM EDTA). The purified M.BstYI protein was analyzed on SDS-PAGE and found to be in the correct size of 36.9 kDa. The M.BstYI protein was partially active in modifying lambda DNA in vivo. Because the M.BstYI protein concentration was low, resulting in only partial BstYI site modification. In order to increase the level of M.BstYI expression, the expression vector was introduced into two *E. coli* K strain T7 expression hosts RR1 (λDE3) and ER1821 (λDE3). The expression level in the K-12 strains was significantly higher than that in the B strain ER2566. Three L of RR1 (λDE3) [TYB2-BstYIM] and 3 L of ER1821 (λDE3) [TYB2 -BstYIM] cells were cultured and induced with IPTG and about 12 g of cells were obtained. Six grams of cells were lysed for the purification of M.BstYI.

9. Purification of M.BstYI by Chromatography

Figure 6:
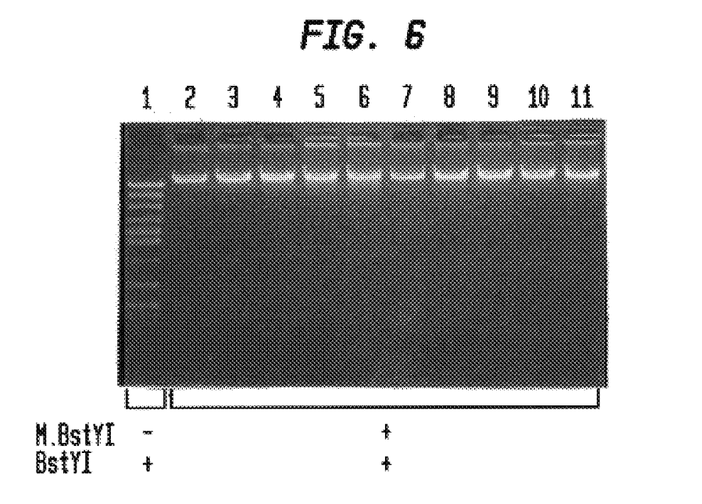
FIG. 6. Recombinant BstYI methylase activity in purified fractions. Lane 1, control, lambda DNA cleaved by BstYI endonuclease; lanes 2 to 11, lambda DNA was first modified by M.BstYI for 1 h and then treated with BstYI endonuclease for 1 h. Lanes 2 to 6, purified M.BstYI from lot 2A; Lanes 7 to 11, purified M.BstYI from lot 2B. After methylation of BstYI sites, the DNA substrate was resistant to BstYI digestion.
Figure 7:
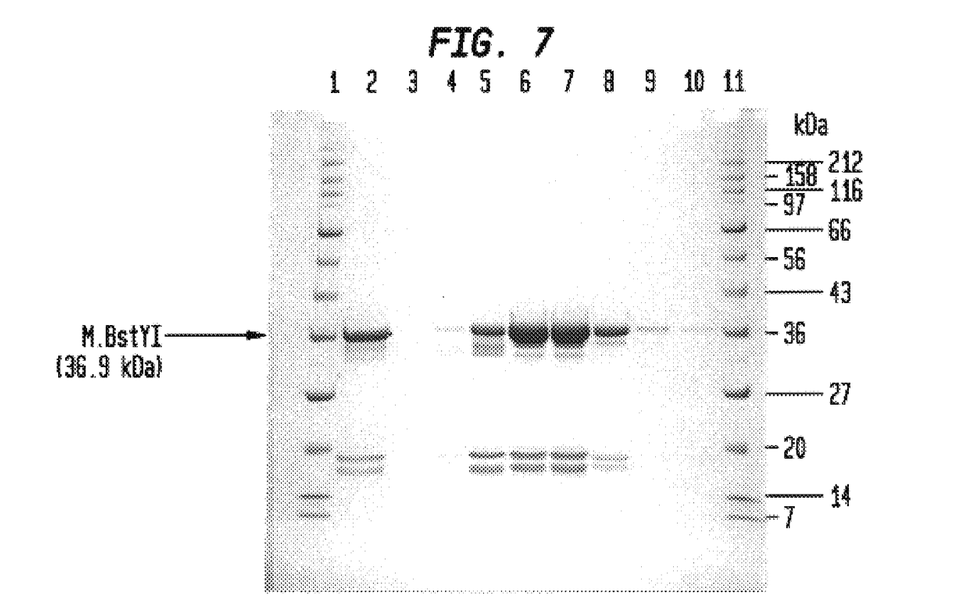
FIG. 7. Purified recombinant M.BstYI protein. Lanes 1 and 11, protein size marker; lane 2, purified M.BstYI protein after Heparin 5PW column; lane 3, flow-through of Heparin 5PW column; lanes 4 to 10, M.BstYI-containing fractions from a Source S column. The predicted and observed molecular mass of M.BstYI was 36.9 kDa.

The cell extract containing M.BstYI was loaded onto a chitin column (53 ml) that had been equilibrated with buffer of 0.5 M NaCl, 20 mM Tris-HCl, pH 7.6, 0.1 mNM EDTA. After extensive washing of the column with the column buffer (0.5 M NaCl, 20 mM Tris-HCl, pH 7.6, 0.1 mM EDTA), the column was flooded with 150 ml of 0.5 M NaCl and 40 mM DTT. The column was left at 40° C. overnight for DTT-facilitated cleavage of the fusion protein. The cleaved product of M.BstYI was eluted with column buffer and 10 ml of fractions were collected. The fractions with high protein concentration were assayed on lambda DNA for methylase activity. Following the methylation reaction, the DNA was subjected to BstYI digestion. It was found that fractions 1–8 contained active M.BstYI. The active M.BstYI fractions (approximately 20 mg protein) were pooled and dialyzed in a buffer containing 50 mM NaCl, 20 mM Tris-HCl, pH 7.6, 0.1 mM EDTA, 1 mM DTT at 40° C. overnight. The protein was loaded onto a Source Q column. The column was washed extensively with the low salt buffer. Protein was eluted with a gradient of 50 mm to 1 M NaCl. Fractions 5–12 were analyzed by SDS-PAGE and the M.BstYI protein band was detected with at least 90% purity. The active fractions were pooled and dialyzed into enzyme storage buffer (50 mM NaCl, 10 mM Tris-HCl, 0.1 mM EDTA, 1 mM DTT, 50% Glycerol (pH 7.6 at 4° C). The protein was loaded onto a Heparin TSK 5PW column and washed with the low salt buffer (0.1 M NaCl, 20 mM $KPO_4$, 0.1 mM EDTA, 1 mM DTT) and was eluted with a NaCl gradient of 0.1 M to 1 M. Half of the Heparin TSK 5PW pool was dialyzed into enzyme storage buffer (above) and was labeled lot 2A. The remaining half was heated at 60° C. for 20 min. and was further purified through a Heparin TSK 5PW column and through a Source S column, and was dialyzed into enzyme storage buffer resulting in the purified product for lot 2B. Both preparations contained M.BstYI with >90% purity and lack non-specific endonuclease and exonuclease. The protein gel is shown in FIG. 7. The result of M.BstYI activity assay was shown in FIG. 6. Lambda DNA was first modified by M.BstYI in a methylation buffer (50 mM Tris-HCl, pH 7.5, 10 mM EDTA, 5 mM DTT, 80 $\mu$M S-adenosyl-methionine (SAM)) for one h at 60° C. or 37° C. After methylation of the substrate, the DNA was cleaved with BstYI in its restriction buffer containing 10 mm Tris-HCl, pH 7.5, 10 mM $MgCl_2$, and 1 mM DTT. When the DNA was modified by M.BstYI, the DNA was resistant to BstYI digestion As shown in FIG. 6. Lot 2A and 2B had 15 ml and 8 ml of purified M.BstYI respectively. The methylase activity was about 60,000–80,000 units/ml. So the final M.BstYI yield was approximately $1.4 \times 10^6$ units from 6 grams of IPTG-induced cells.

10. Cloning of bstYIR Gene by Inverse PCR

Two primers were synthesized with the following sequence:

5' tattcgcatttgaacgggttggaa 3' (244-89) (SEQ ID NO:9)
5' tacttcaacaattctcatatctacact 3' (244-90) (SEQ ID NO:10)

The Genomic DNA was digested with AciI, BfaI, BspHI, EcoRI, HhaI, HpyIV, MseI, and NlaIIII. The digested DNA was ligated at a low DNA concentration at 2 $\mu$g/ml and then used for inverse PCR amplification of BstYR gene. Inverse PCR conditions were 94° C. 1 min, 55° C. 1 min, 72° C. 1 min for 35 cycles. Inverse PCR products were derived from BfaI, BspHI, HpyIV, MseI, and NlaIIII templates, gel-purified from low-melting agarose and sequenced using primers 244-89 and 244-90. An ORF of 612 bp was found downstream of the bstYIM gene. This ORF was named bstYIR gene. It encodes a 203-aa protein with predicted molecular mass of 23 kDa.

11. Expression of bstYIR Gene in T7 Expression Vector pET21b

Since there is an NdeI site in the bstYIR gene, the NdeI site cannot be used for cloning of bstYIR gene into pET21b expression vector. Two restriction sites (XbaI site and XhoI site) were incorporated into the forward and reverse primers, respectively. Two primers were synthesized to amplify the bstYIR gene by PCR. The primers had the following sequence:

5' ttttattctagaggaggtaaataaatgagaattgttgaagtatattcgcat 3' (244-191) (SEQ ID NO:11)
5' ccttctttcctcgagttaatttataccttataatactaacat 3' (244-192) (SEQ ID NO:12)

The bstYIR gene was amplified by PCR using Vent® DNA polymerase and primers 244-191 and 244-192 under conditions of 94° C. 1 min, 55° C. 1 min, 72° C. 1 min for 25 cycles. The PCR product was purified by Qiagen spin column and digested with XbaI and XhoI. After DNA purification, the PCR DNA was ligated to pET21b with compatible ends. The ligated DNA was transformed into premodified host ER2744 [pACYC-BstYIM] and selected for $Ap^R$ $Cm^R$ transformants. Among 36 plasmid mini-preparation, 7 clones carried the desired insert. All 7 clones were cultured in 10 ml LB plus Ap and Cm and induced with IPTG (0.5 mM final) for 3 h. Cell extracts were prepared and assayed for BstYI activity. One clone #11 displayed high BstYI activity. The yield was approximately $10^6$ units /gram of cells. However, this expression clone was not stable because it lost activity after subculture of cell stocks (cell stock was stored at −20° C. in 50% glycerol). The reason of instability was probably due to the high level of expression under non-induced conditions. When uninduced and IPTG-induced cell extracts were analyzed by SDS-PAGE, both displayed similar level of BstYI endonuclease production. The bstYIR gene was inserted into the XbaI and XhoI sites of pET21b. The XbaI site is 3-bp away from the lac operator sequence that Lac repressor binds. For some unknown reason, the insertion of bstYIR gene in the XbaI site interfered with Lac repression.

12. Elimination of an Internal NdeI Site in bstYIR Gene and Expression of bstYIR Gene in the T7 Expression Vector pET21at The bstYIR gene was cloned into pET21at using restriction sites NdeI and XhoI. Overhang extension PCR mutagenesis was used as part of the cloning procedure to remove the internal NdeI site thus introducing a silent base-pair change from T to C at position 435 of the gene. In this procedure, the first 449 bp of the gene were amplified using primers:

5' gggagtgtacatatgagaattgttgaagta 3' (250-176) (SEQ ID NO:13) 5' forward
5' aacatagaaagccatgtgtttgacgaaaag 3' (250-177) (SEQ ID NO:14) internal reverse mutagenic The second half of the gene was amplified using the following primers:

5' cttttcgtcaaacacatggctttctatgtt 3' (250-178) (SEQ ID NO: 15) internal forward mutagenic
5' ccttctttcctcgagttaatttataccttataatactaacat 3' (244-192) (SEQ ID NO:16) 3' reverse The two gene segments were individually amplified by Vent® polymerase using 22 cycles of 95° C. 1 min, 58° C. 1 min, 72° C. 1 min. The PCR products were purified from a low-melting agarose gel and then were added to a PCR overhang extension reaction. The PCR overhang extension reaction was amplified by Vent® polymerase using the 5' forward and 3' reverse primers listed above to give the full-length bstYIR gene void of an internal NdeI site. Extension/amplification was carried out for 10 cycles using conditions of 95° C. 1 min, 58° C. 1 min, 72° C. 1 min. The final PCR product was purified by ethanol precipitation and then digested with NdeI and XhoI. After gel purification, the bstYIR gene was ligated to pET21at using compatible restriction sites. The ligated DNA was transformed into pre-modified host ER2744 [pACYC-BstYIM, pCEF8] and transformants were selected on Amp/Cam/Kan—LB plates (plasmid pCEF8 carries pSC101 origin and T7 lysozyme gene whose product inhibits T7 RNA polymerase activity).

Figure 1:
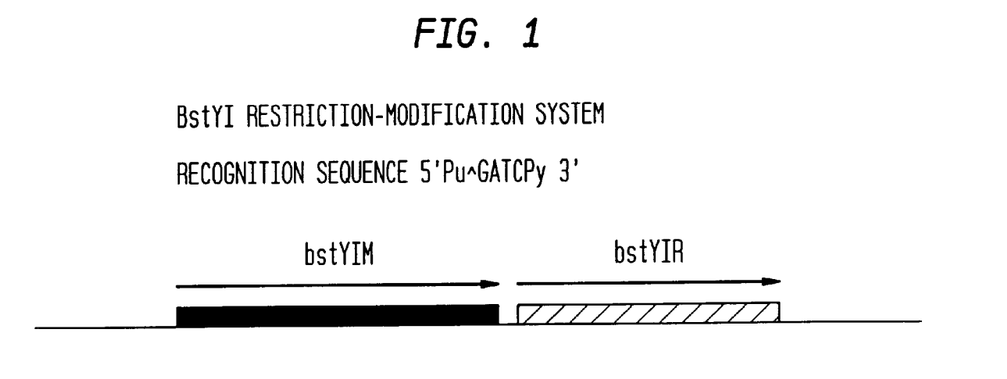
FIG. 1. Gene organization of BstYI restriction-modification system. bstYIR, BstYI restriction endonuclease gene; bstYIM, BstYI methylase gene.
Figure 3:
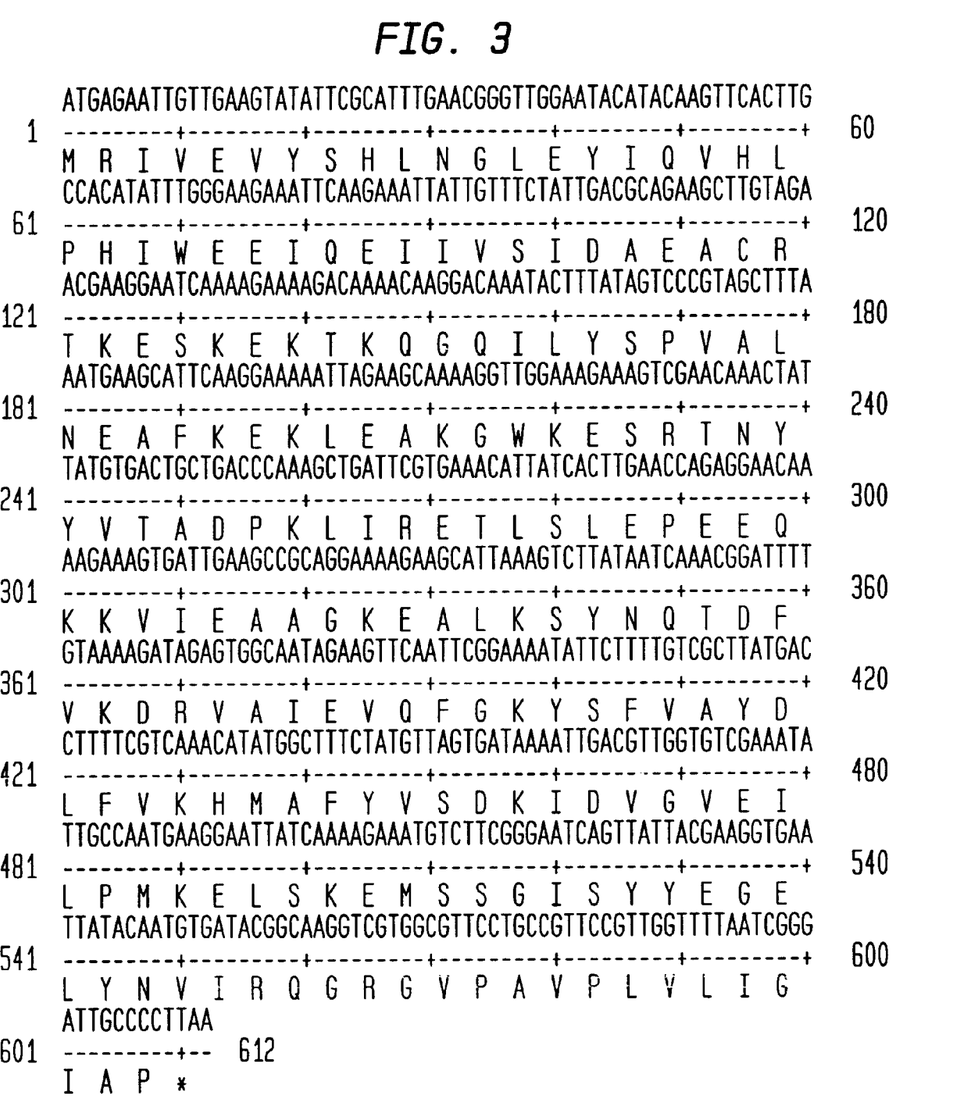
FIG. 3. DNA sequence of BstYI endonuclease gene (SEQ ID NO:3) (bstYIR, 612 bp) and its encoded amino acid sequence (SEQ ID NO:4).
Figure 4:
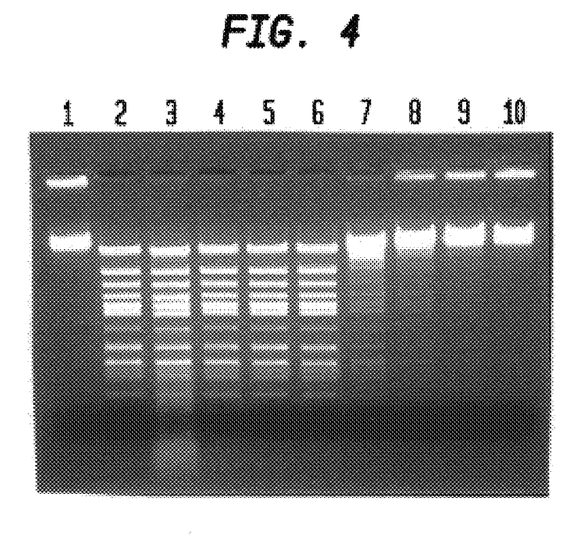
FIG. 4. Recombinant BstYI endonuclease activity in cell extract. Lane 1, uncut lambda DNA; lane 2, lambda DNA cut by purified native BstYI; lanes 3 to 10, lambda DNA treated with cell extract containing recombinant BstYI restriction endonuclease; The dilution factors in lanes 3–10: $10^{-1}$, $10^{-2}$, $10^{-3}$, $10^{-4}$, $2\times10^{-5}$, $1\times10^{-5}$, $5\times10^{-6}$, $2\times10^{-6}$.
Figure 5:
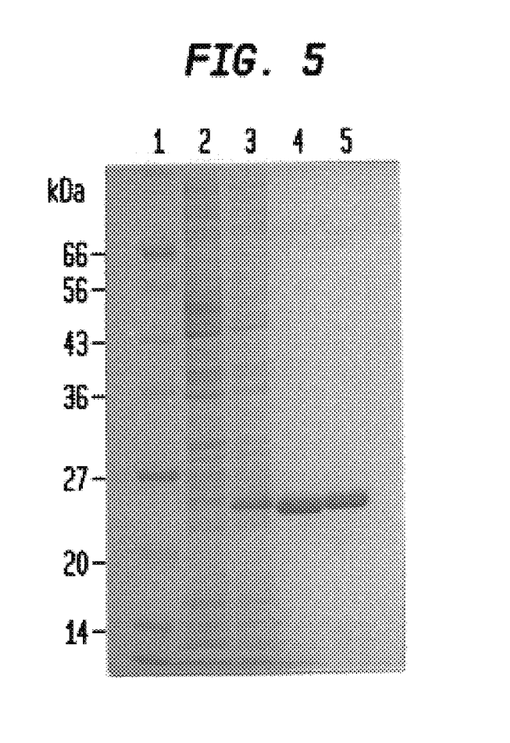
FIG. 5. Purified recombinant BstYI endonuclease. Lane 1, protein size marker; lanes 2 and 3, uninduced and IPTG-induced cell extracts; lanes 4 and 5, purified BstYI restriction endonuclease after Heparin Sepharose and DEAE Sepharose columns. The predicted and observed molecular mass of BstYI endonuclease was 23 kDa.

Plasmid DNA was prepared from 36 transformants by Qiagen spin columns and 15 clones carried the desired insert. All 15 clones were cultured in 10 ml LB plus Amp (100 ug/ml), Cam (33ug/ml) and Kan (50 ug/ml) and induced with IPTG (0.5 mM final) for 3 hours at 30° C. Cell extracts were prepared and assayed for BstYI activity. Of those 15 clones, 12 exhibited high BstYI activity. Clone #20 was grown in large-scale (3 Liters) and an assay of the cell extract determined the activity to be $2.4 \times 10^7$ units per gram of cells. Consistent with this high activity, SDS-PAGE analysis of the cell extract of the IPTG-induced culture revealed an overexpressed protein of approximately 23 kDa (see FIG. 5).

The E. coli strain ER2744 [pACYC-BstYIM, pET21at-BstYIR, pCEF8] has been deposited with the American Type Culture Collection on Jan. 24, 2001 and received ATCC Accession No. PTA-2864.

13. Purification of BstYI Endonuclease to Homogeneity

Cell extract was prepared by sonication of 12.0 grams of IPTG-induced cells resuspended in 60 ml sonication buffer (20 mM $KPO_4$ pH 6.8, 10 mM β-mercaptoethanol, 0.1 mM EDTA). After sonication, 50 mM NaCl was added to the cell extract followed by heating at 65° C. for 30 min to denature E. coli proteins. The heated extract was centrifuged at 15,000 rpm for 30 min and the clarified supernatant was retained (57 ml). Glycerol was added to give a final concentration of 5% before loading the supernatant onto a Heparin Sepharose column equilibrated with 20 mM $KPO_4$ pH 6.8, 50 mM NaCl, 10 mM β-ME, 0.1 mM EDTA and 5% glycerol. Fractions were eluted with a NaCl gradient from 0.05 M–0.8 M. Fractions containing BstYI endonuclease as determined by an activity assay were pooled and dialyzed overnight in DEAE-Sepharose loading buffer (20 mM Tris-HCl, pH 7.5, 50 mM NaCl, 10 mM β-mercaptoethanol, 0.1 mM EDTA and 5% glycerol). After dialysis, 72 ml were loaded onto a DEAE Sepharose column equilibrated with the same buffer. Fractions were eluted with a 0.05 M–0.6 M NaCl gradient and those fractions containing purified BstYI as determined by SDS-PAGE analysis were pooled. The final pool of 20 ml BstYI contained a protein concentration of 0.75 mg/ml as determined by the Bradford Assay (Bio-Rad). The purified protein was analyzed by SDS-PAGE and estimated to be more than 98% pure.

What is claimed is:

1. Isolated DNA coding for the BstYI restriction endonuclease, wherein the isolated DNA is obtainable from *Bacillus stearothermophilus* Y406.

2. A recombinant DNA cloning vector comprising a vector into which a DNA segment encoding the BstYI restriction endonuclease has been inserted.

3. Isolated DNA encoding the BstYI restriction endonuclease and BstY methylase, wherein the isolated DNA is obtainable from ATCC No. PTA-2864.

4. A cloning vector which comprises the isolated DNA of claim 3.

5. A host cell transformed by the cloning vector of claims 2 or 4.

6. A method of producing recombinant BstY restriction endonuclease comprising culturing a host cell transformed with the vector of claims 2 or 4 under conditions suitable for expression of said endonuclease and methylase.

* * * * *

UNITED STATES PATENT AND TRADEMARK OFFICE
CERTIFICATE OF CORRECTION

PATENT NO.   : 6,403,354 B1
DATED        : June 11, 2002
INVENTOR(S)  : Xu et al.

It is certified that error appears in the above-identified patent and that said Letters Patent is hereby corrected as shown below:

Column 6,
Line 12, replace "M.BStYI" with -- M.BstYI --
Line 13, replace "Itein" with -- intein --
Line 61, replace "mA" with -- MA --

Column 7,
Line 1, replace "BStYI" with -- BstYI --

Column 8,
Line 35, replace ""BClI" with -- BclI --
Line 43, replace "AP$^R$" with -- Ap$^R$ --
Line 51, replace "AP$^R$" with -- Ap$^R$ --

Column 9,
Line 44, replace "endonuclase" with -- endonuclease --

Column 11,
Line 11, replace "mm" with -- mM --
Line 34, replace "mm" with -- mM --

Signed and Sealed this

Twenty-ninth Day of October, 2002

Attest:

JAMES E. ROGAN
Attesting Officer          Director of the United States Patent and Trademark Office

SEQUENCE LISTING

<160> NUMBER OF SEQ ID NOS: 16

<210> SEQ ID NO 1
<211> LENGTH: 957
<212> TYPE: DNA
<213> ORGANISM: Bacillus stearothermophilus Y406
<220> FEATURE:
<221> NAME/KEY: CDS
<222> LOCATION: (1)..(954)

<400> SEQUENCE: 1

```
atg aac ttc ttg agt cta ttt gaa tat aga a tt gat gat gtt tat aag      48
Met Asn Phe Leu Ser Leu Phe Glu Tyr Arg I le Asp Asp Val Tyr Lys
 1               5                   10                  15 gaa gat agc gaa att gta ttt cat aac ggc g at gcg ctt gag ttt ttg      96
Glu Asp Ser Glu Ile Val Phe His Asn Gly A sp Ala Leu Glu Phe Leu
             20                  25                  30 aaa aca tta ccc gat aat ctt gtg aaa tta g cg atc acg tcc ccg cct    144
Lys Thr Leu Pro Asp Asn Leu Val Lys Leu A la Ile Thr Ser Pro Pro
         35                  40                  45 tat aac gtt ggt aag tct tat gaa gta aaa a cg tca gtt gaa gaa tat    192
Tyr Asn Val Gly Lys Ser Tyr Glu Val Lys T hr Ser Val Glu Glu Tyr
     50                  55                  60 ctt gca aca caa gaa gcc gta att gaa gaa t tg att cgg gtc gtt gat    240
Leu Ala Thr Gln Glu Ala Val Ile Glu Glu L eu Ile Arg Val Val Asp
 65                  70                  75                  80 gat cac gga agc att tgt tgg caa gtg gga a ac tat gtt aat aaa gga    288
Asp His Gly Ser Ile Cys Trp Gln Val Gly A sn Tyr Val Asn Lys Gly
                 85                  90                  95 gaa att ttt ccg ctt gat ata ttt tat tat c aa atc ttc aaa aaa cat    336
Glu Ile Phe Pro Leu Asp Ile Phe Tyr Tyr G ln Ile Phe Lys Lys His
            100                 105                 110 ggt ttg aaa ctt cgg aac cgt atc att tgg c at ttt ggt cac ggt ctt    384
Gly Leu Lys Leu Arg Asn Arg Ile Ile Trp H is Phe Gly His Gly Leu
        115                 120                 125 cac gca aag aaa cgc ttt tcg gga aga tat g ag aca ttg ctt tgg ttc    432
His Ala Lys Lys Arg Phe Ser Gly Arg Tyr G lu Thr Leu Leu Trp Phe
    130                 135                 140
```

```
acg aaa tca gat gat tac act ttt aac ctt g ac ccc gtt cgg gtt cct      480
Thr Lys Ser Asp Asp Tyr Thr Phe Asn Leu A sp Pro Val Arg Val Pro
145                 150                 155                 160 gca aag tat ccc ggc aaa cgt cat tat aaa g gt gac aaa aaa ggc gaa      528
Ala Lys Tyr Pro Gly Lys Arg His Tyr Lys G ly Asp Lys Lys Gly Glu
                165                 170                 175 cta tcg ggg aat ccg aaa gga aaa aat cct t cg gac gta tgg gaa ttc      576
Leu Ser Gly Asn Pro Lys Gly Lys Asn Pro S er Asp Val Trp Glu Phe
            180                 185                 190 gtt gtt caa gaa tgg gac aag gaa ctt tgg g aa att ccg aac gtg aag      624
Val Val Gln Glu Trp Asp Lys Glu Leu Trp G lu Ile Pro Asn Val Lys
        195                 200                 205 gcg aat cac ccc gaa aaa aca att cac ccg t gt caa tat ccg att gaa      672
Ala Asn His Pro Glu Lys Thr Ile His Pro C ys Gln Tyr Pro Ile Glu
    210                 215                 220 ttg gtt gaa cgt tgt gtt tta gca tta acg a at gaa aat gac ttt gtt      720
Leu Val Glu Arg Cys Val Leu Ala Leu Thr A sn Glu Asn Asp Phe Val
225                 230                 235                 240 ctt gac ccg tat gcg ggt gtt ggt tcg tcg t tg att ggt gca ttg aaa      768
Leu Asp Pro Tyr Ala Gly Val Gly Ser Ser L eu Ile Gly Ala Leu Lys
                245                 250                 255 cat gga aga aaa gca atc ggt gtt gat aaa g ag aaa gaa tac gtt gag      816
His Gly Arg Lys Ala Ile Gly Val Asp Lys G lu Lys Glu Tyr Val Glu
            260                 265                 270 att gga aaa caa aga atc aaa gat ttc tat g ac ggt aaa tta aag att      864
Ile Gly Lys Gln Arg Ile Lys Asp Phe Tyr A sp Gly Lys Leu Lys Ile
        275                 280                 285 aga ccg tta gga aaa ccc gtt tac caa cca a cg gga aga gaa aag gtt      912
Arg Pro Leu Gly Lys Pro Val Tyr Gln Pro T hr Gly Arg Glu Lys Val
    290                 295                 300 gca caa att cct gaa gaa tgg aaa gaa ctc c ta gaa caa aag taa        9 57
Ala Gln Ile Pro Glu Glu Trp Lys Glu Leu L eu Glu Gln Lys
305                 310                 315

<210> SEQ ID NO 2
<211> LENGTH: 318
<212> TYPE: PRT
<213> ORGANISM: Bacillus stearothermophilus Y406

<400> SEQUENCE: 2

Met Asn Phe Leu Ser Leu Phe Glu Tyr Arg I le Asp Asp Val Tyr Lys
1               5                   10                  15

Glu Asp Ser Glu Ile Val Phe His Asn Gly A sp Ala Leu Glu Phe Leu
            20                  25                  30

Lys Thr Leu Pro Asp Asn Leu Val Lys Leu A la Ile Thr Ser Pro Pro
        35                  40                  45

Tyr Asn Val Gly Lys Ser Tyr Glu Val Lys T hr Ser Val Glu Glu Tyr
    50                  55                  60

Leu Ala Thr Gln Glu Ala Val Ile Glu Glu L eu Ile Arg Val Val Asp
65                  70                  75                  80

Asp His Gly Ser Ile Cys Trp Gln Val Gly A sn Tyr Val Asn Lys Gly
                85                  90                  95

Glu Ile Phe Pro Leu Asp Ile Tyr Tyr Gln I le Phe Lys Lys His
            100                 105                 110

Gly Leu Lys Leu Arg Asn Arg Ile Ile Trp H is Phe Gly His Gly Leu
        115                 120                 125

His Ala Lys Lys Arg Phe Ser Gly Arg Tyr G lu Thr Leu Leu Trp Phe
    130                 135                 140
```

-continued

```
Thr Lys Ser Asp Asp Tyr Thr Phe Asn Leu Asp Pro Val Arg Val Pro
145                 150                 155                 160

Ala Lys Tyr Pro Gly Lys Arg His Tyr Lys Gly Asp Lys Lys Gly Glu
                165                 170                 175

Leu Ser Gly Asn Pro Lys Gly Lys Asn Pro Ser Asp Val Trp Glu Phe
            180                 185                 190

Val Val Gln Glu Trp Asp Lys Glu Leu Trp Glu Ile Pro Asn Val Lys
        195                 200                 205

Ala Asn His Pro Glu Lys Thr Ile His Pro Cys Gln Tyr Pro Ile Glu
    210                 215                 220

Leu Val Glu Arg Cys Val Leu Ala Leu Thr Asn Glu Asn Asp Phe Val
225                 230                 235                 240

Leu Asp Pro Tyr Ala Gly Val Gly Ser Ser Leu Ile Gly Ala Leu Lys
                245                 250                 255

His Gly Arg Lys Ala Ile Gly Val Asp Lys Glu Lys Glu Tyr Val Glu
            260                 265                 270

Ile Gly Lys Gln Arg Ile Lys Asp Phe Tyr Asp Gly Lys Leu Lys Ile
        275                 280                 285

Arg Pro Leu Gly Lys Pro Val Tyr Gln Pro Thr Gly Arg Glu Lys Val
    290                 295                 300

Ala Gln Ile Pro Glu Glu Trp Lys Glu Leu Leu Glu Gln Lys
305                 310                 315
```

<210> SEQ ID NO 3
<211> LENGTH: 612
<212> TYPE: DNA
<213> ORGANISM: Bacillus stearothermophilus Y406
<220> FEATURE:
<221> NAME/KEY: CDS
<222> LOCATION: (1)..(609)

<400> SEQUENCE: 3

```
atg aga att gtt gaa gta tat tcg cat ttg aac ggg ttg gaa tac ata      48
Met Arg Ile Val Glu Val Tyr Ser His Leu Asn Gly Leu Glu Tyr Ile
 1               5                  10                  15 caa gtt cac ttg cca cat att tgg gaa gaa att caa gaa att att gtt      96
Gln Val His Leu Pro His Ile Trp Glu Glu Ile Gln Glu Ile Ile Val
                20                  25                  30 tct att gac gca gaa gct tgt aga acg aag gaa tca aaa gaa aag aca     144
Ser Ile Asp Ala Glu Ala Cys Arg Thr Lys Glu Ser Lys Glu Lys Thr
            35                  40                  45 aaa caa gga caa ata ctt tat agt ccc gta gct tta aat gaa gca ttc     192
Lys Gln Gly Gln Ile Leu Tyr Ser Pro Val Ala Leu Asn Glu Ala Phe
        50                  55                  60 aag gaa aaa tta gaa gca aaa ggt tgg aaa gaa agt cga aca aac tat     240
Lys Glu Lys Leu Glu Ala Lys Gly Trp Lys Glu Ser Arg Thr Asn Tyr
 65                  70                  75                  80 tat gtg act gct gac cca aag ctg att cgt gaa aca tta tca ctt gaa     288
Tyr Val Thr Ala Asp Pro Lys Leu Ile Arg Glu Thr Leu Ser Leu Glu
                85                  90                  95 cca gag gaa caa aag aaa gtg att gaa gcc gca gga aaa gaa gca tta     336
Pro Glu Glu Gln Lys Lys Val Ile Glu Ala Ala Gly Lys Glu Ala Leu
                100                 105                 110 aag tct tat aat caa acg gat ttt gta aaa gat aga gtg gca ata gaa     384
Lys Ser Tyr Asn Gln Thr Asp Phe Val Lys Asp Arg Val Ala Ile Glu
            115                 120                 125 gtt caa ttc gga aaa tat tct ttt gtc gct tat gac ctt ttc gtc aaa     432
Val Gln Phe Gly Lys Tyr Ser Phe Val Ala Tyr Asp Leu Phe Val Lys
```

```
         130                 135                 140
cat atg gct ttc tat gtt agt gat aaa att g ac gtt ggt gtc gaa ata        480
His Met Ala Phe Tyr Val Ser Asp Lys Ile A sp Val Gly Val Glu Ile
145                 150                 155                 160 ttg cca atg aag gaa tta tca aaa gaa atg t ct tcg gga atc agt tat        528
Leu Pro Met Lys Glu Leu Ser Lys Glu Met S er Ser Gly Ile Ser Tyr
                165                 170                 175 tac gaa ggt gaa tta tac aat gtg ata cgg c aa ggt cgt ggc gtt cct        576
Tyr Glu Gly Glu Leu Tyr Asn Val Ile Arg G ln Gly Arg Gly Val Pro
                180                 185                 190 gcc gtt ccg ttg gtt tta atc ggg att gcc c ct taa                        612
Ala Val Pro Leu Val Leu Ile Gly Ile Ala P ro
                195                 200

<210> SEQ ID NO 4
<211> LENGTH: 203
<212> TYPE: PRT
<213> ORGANISM: Bacillus stearothermophilus Y406

<400> SEQUENCE: 4

Met Arg Ile Val Glu Val Tyr Ser His Leu A sn Gly Leu Glu Tyr Ile
  1               5                  10                  15

Gln Val His Leu Pro His Ile Trp Glu Glu I le Gln Glu Ile Ile Val
                 20                  25                  30

Ser Ile Asp Ala Glu Ala Cys Arg Thr Lys G lu Ser Lys Glu Lys Thr
             35                  40                  45

Lys Gln Gly Gln Ile Leu Tyr Ser Pro Val A la Leu Asn Glu Ala Phe
         50                  55                  60

Lys Glu Lys Leu Glu Ala Lys Gly Trp Lys G lu Ser Arg Thr Asn Tyr
 65                  70                  75                  80

Tyr Val Thr Ala Asp Pro Lys Leu Ile Arg G lu Thr Leu Ser Leu Glu
                 85                  90                  95

Pro Glu Glu Gln Lys Lys Val Ile Glu Ala A la Gly Lys Glu Ala Leu
            100                 105                 110

Lys Ser Tyr Asn Gln Thr Asp Phe Val Lys A sp Arg Val Ala Ile Glu
        115                 120                 125

Val Gln Phe Gly Lys Tyr Ser Phe Val Ala T yr Asp Leu Phe Val Lys
    130                 135                 140

His Met Ala Phe Tyr Val Ser Asp Lys Ile A sp Val Gly Val Glu Ile
145                 150                 155                 160

Leu Pro Met Lys Glu Leu Ser Lys Glu Met S er Ser Gly Ile Ser Tyr
                165                 170                 175

Tyr Glu Gly Glu Leu Tyr Asn Val Ile Arg G ln Gly Arg Gly Val Pro
                180                 185                 190

Ala Val Pro Leu Val Leu Ile Gly Ile Ala P ro
                195                 200

<210> SEQ ID NO 5
<211> LENGTH: 54
<212> TYPE: DNA
<213> ORGANISM: Bacillus stearothermophilus Y406

<400> SEQUENCE: 5
aaaactggat ccggaggtaa aaaaatgaac ttcttgagtc tatttgaata t aga            54

<210> SEQ ID NO 6
<211> LENGTH: 42
<212> TYPE: DNA
```

<213> ORGANISM: Artificial Sequence
<220> FEATURE:
<223> OTHER INFORMATION: Description of Artificial Sequence: synthetic organism

<400> SEQUENCE: 6
taacacgcat gcttactttt gttctaggag ttctttccat tc          42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: synthetic organism

<400> SEQUENCE: 7
gtagtgaggc atatgaactt cttgagtcta tttgaatata ga          42

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: synthetic organism

<400> SEQUENCE: 8
cttttgttct aggagttctt tccattc                           27

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: synthetic organism

<400> SEQUENCE: 9
tattcgcatt tgaacgggtt ggaa                              24

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: synthetic organism

<400> SEQUENCE: 10
tacttcaaca attctcatat ctacact                           27

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: synthetic organism

<400> SEQUENCE: 11
ttttattcta gaggaggtaa ataaatgaga attgttgaag tatattcgca t    51

<210> SEQ ID NO 12
<211> LENGTH: 42
<212> TYPE: DNA
<213> ORGANISM: Artificial Sequence

```
<220> FEATURE:
<223> OTHER INFORMATION: Description of Artificial  Sequence: synthetic
      organism

<400> SEQUENCE: 12
ccttctttcc tcgagttaat ttataccta taatactaac at                              42

<210> SEQ ID NO 13
<211> LENGTH: 30
<212> TYPE: DNA
<213> ORGANISM: Artificial Sequence
<220> FEATURE:
<223> OTHER INFORMATION: Description of Artificial  Sequence: synthetic
      organism

<400> SEQUENCE: 13
gggagtgtac atatgagaat tgttgaagta                                          30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial  Sequence: synthetic
      organism

<400> SEQUENCE: 14
aacatagaaa gccatgtgtt tgacgaaaag                                          30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial  Sequence: synthetic
      organism

<400> SEQUENCE: 15
cttttcgtca aacacatggc tttctatgtt                                          30

<210> SEQ ID NO 16
<211> LENGTH: 42
<212> TYPE: DNA
<213> ORGANISM: Artificial Sequence
<220> FEATURE:
<223> OTHER INFORMATION: Description of Artificial  Sequence: synthetic
      organism

<400> SEQUENCE: 16
ccttctttcc tcgagttaat ttataccta taatactaac at                              42
```